United States Patent [19]

Imai

[11] Patent Number: 5,165,964

[45] Date of Patent: Nov. 24, 1992

[54] PROCESS FOR APPLYING DEODORANT PARTICLES TO A MEMBRANE

[75] Inventor: Takashi Imai, Okayama, Japan

[73] Assignee: Junkosha Co., Ltd., Tokyo, Japan

[21] Appl. No.: 718,070

[22] Filed: Jun. 20, 1991

[51] Int. Cl.⁵ .............................................. B05D 5/00
[52] U.S. Cl. .................................... 427/245; 424/404
[58] Field of Search ............................... 427/244–246, 427/2; 424/404

[56] References Cited

U.S. PATENT DOCUMENTS

| | | | |
|---|---|---|---|
| 2,121,604 | 6/1938 | Lynch et al. | 424/404 X |
| 3,524,755 | 8/1970 | Hochberg | 427/245 |
| 4,069,086 | 1/1978 | Reif | 427/2 X |
| 5,037,412 | 8/1991 | Tanzer et al. | 604/359 |
| 5,041,467 | 8/1991 | Kataoka et al. | 521/99 |

Primary Examiner—Evan Lawrence
Attorney, Agent, or Firm—Gary A. Samuels

[57] ABSTRACT

A process for applying deodorant particles to a membrane used for clothing in which the particles are applied from a liquid coating material that penetrates into the pores of the membrane, thus resulting in a higher concentration of particles in the surface coating than in the liquid coating material.

4 Claims, No Drawings

PROCESS FOR APPLYING DEODORANT PARTICLES TO A MEMBRANE

FIELD OF THE INVENTION

The invention relates to a process for applying deodorant particles to a membrane used for clothing.

BACKGROUND OF THE INVENTION

Owing to the fact that liquid water-penetrating resistant, water vapor permeable clothing not only prevents the penetration and adhesion of rainwater, but also allows the vapor produced from perspiration to permeate the cloth, such cloth is highly adapted for manufacture of clothing which is comfortable to wear in continuous heavy service. Various examples of such clothing that have been liquid-coated with polyurethane or laminated with microporous polytetrafluoroethylene (PTFE) film have been illustrated in Japanese Patent Publication Nos. 58-38456, 60-47955 and 60-39014.

Cloth produced according to the methods above can be supplied for use in clothing adapted for comfortable wear without causing the wearer any feeling of stuffiness when the wearer perspires. This is based on the fact that the clothing is waterproof and water vapor permeable, allowing water vapor permeation therethrough. However, when the clothing is worn in surroundings where unpleasant odors are present, such as the farming and dairy industries, malodorous components end up adhering to the skin of the worker. Even after the worker's job has ended, said odors emanate from the body and underwear of said worker, and naturally cause discomfort to those in the worker's immediate surroundings. The penetration and adhesion of malodorous components cannot be prevented in the case of clothing utilizing water vapor permeable sheets of the above type.

SUMMARY OF THE INVENTION

The present invention comprises a process for concentrating deodorant particles in a surface coating covering a membrane having continuous pores from one side of the membrane to the other, which comprises (a) applying a surface coating of a liquid coating material that contains particulate deodorant particles, said particles having an average diameter of about 1 micron, to at least one side of a membrane having continuous pores whose openings are too small to allow passage into the pores of the deodorant particles; and (b) allowing the liquid coating material to penetrate at least partially into the pores of the membrane, thus resulting in a greater concentration of particles in the resulting surface coating than in the originally applied coating material.

DESCRIPTION OF THE PREFERRED EMBODIMENTS

It has been found that hydrophilic resins containing a particulate deodorant material mixed uniformly therein can be coated on a microporous polymer membrane, such as microporous polyolefins or preferably microporous PTFE membrane. The hydrophilic resin penetrates the pores of the microporous membrane at least partially, leaving the resin layer on the surface of the membrane rich in particulate deodorant material. The reason for this is that the deodorant material molecules are an average of about 1 micron in diameter so that it ordinarily does not penetrate the pores of the membrane, which are usually about 0.2 micron or smaller in size. The coated-on deodorant particles thus tend to concentrate in the outer portion of the hydrophilic resin layer. The concentration of deodorant particles in the surface resin may be as much as about 3 times its concentration in the original hydrophilic resin coating mixture to give a membrane having a highly concentrated deodorant layer and thus a superior deodorizing function.

When PTFE is the microporous membrane, it can be obtained as a material in which countless fine fibers are formed in a spider web-like pattern between micronodes by fibrillating a PTFE sheet by rolling or drawing or by using both together. Membranes having the following specifications can be employed: porosity 50 to 95%, maximum pore size 0.1 to 3 microns with about 0.2 to 1 micron being preferred; thickness 10 to 200 microns.

Polyether polyurethane resin or polymeric perfluorosulfonic acid or the like are useful as the hydrophilic resin.

A particulate deodorant, such as a metallic oxide (such as copper oxide or iron oxide), a metallic hydroxide such as magnesium hydroxide, a metallic salt (such as phthalocyanine salt), and an organic acid (such as an aliphatic or aromatic carboxylic acid) in the amount of 5–100 g/m$^2$ of a mixture of 1–200 parts by weight per 100 parts by weight of the hydrophilic resin is then coated onto the microporous PTFE membrane. The mixture can be applied by spraying, brushing, or roll-coating. The deodorant particle size is about 1 micron or larger.

EXAMPLE 1

A membrane was prepared by coating a mixture of 30 parts by weight of a copper oxide-type deodorant blended with 100 parts by weight of a polyether polyurethane resin (a hydrophilic resin) onto a microporous PTFE membrane which was obtained by a drawing process such that the maximum pore size was approximately 0.2 micron, the porosity as high as 80%, and the thickness approximately 35 microns.

The water pressure resistance and permeation capacity of the membrane obtained above are shown in Table 1. The membrane had desirable waterproof moisture permeability.

TABLE 1

|  | Capacity | Method of Measurement |
| --- | --- | --- |
| Water Pressure Resistance (kg/cm$^2$) | 3 | JIS L-1092 |
| Moisture Permeability (g/M$^2$ · 24 hr) | 60,000 | JIS L-1099 B Method |

The membrane obtained as above was measured in terms of its deodorizing property vis-a-vis the following malodorous components: ammonia, trimethylamine, and hydrogen sulfide. The methods for measuring this property are as described below.

A) Ammonia 10 microliters of 28% aqueous ammonia was placed in a 300 ml Erlenmeyer flask. After the ammonia had completely vaporized, approximately 1 g. of sample was added thereto and the temperature maintained at 25° C. After 2 hours had elapsed, the residual ammonia concentration in the flask was measured by a Kitagawa-type gas detector.

B) Trimethylamine 10 microliters of an 0.8% trimethylamine aqueous solution was placed in a 300 ml Erlenmeyer flask. Following the same procedure as for ammonia, the residual concentration of trimethylamine in the flask was measured by a Kitagawa-type gas detector.

C) Hydrogen Sulfide

Hydrogen sulfide was formed by placing 1 ml of an 800 ppm hydrogen sulfide aqueous solution and 0.1 ml of 1 N sulfuric acid in a 300 ml rlenmeyer flask, afte which approximately 2 g. of sample was added thereto. The mixture was maintained at 25° C.

After two hours had elapsed, the residual concentration of the hydrogen sulfide in the flask was measured by a Kitagawa-type gas detector.

The results from each of the above measurements are shown in Table 2.

TABLE 2

|  | Ammonia | Trimethylamine | Hydrogen Sulfide |
| --- | --- | --- | --- |
| Blank (ppm) | 6000 | 32 | 140 |
| Sample Film (ppm) | ND | 2.0 | ND |

(ND = not detected)

A fabric was prepared by laminating the above membrane produced according to the present invention with a 40 denier knitted fabric. The properties of this laminated cloth were tested and measured, with the results shown in Table 3. These results confirmed that the sample was waterproof, had moisture permeability desirable for use in all types of work clothes, and had superior deodorizing capabilities.

TABLE 3

| Water Pressure Resistance | 3.0 kg/cm$^2$ | |
| --- | --- | --- |
| Moisture Permeability | 30,000 g/m$^2$ · 24 hours | |
| Deodorizing Capability | | |
| Ammonia | Blank | 6,000 |
|  | Sample | 120 |
| Trimethylamine | Blank | 32 |
|  | Sample | ND |
| Hydrogen Sulfide | Blank | 140 |
|  | Sample | ND |

(ND = not detected)

EXAMPLE 2

A membrane was prepared by coating a mixture of 10 parts by weight of a deodorant agent (Daimushu #6000, manufactured by Dainichiseika Kabushikikaisha) which was mainly composed of Mg(OH)$^2$, blended with 100 parts by weight of a polyether polyurethane resin (a hydrophilic resin) onto a microporous PTFE membrane which was obtained by a drawing process such that the physical properties were the same as those of Example 1.

The water pressure resistance and permeation capacity of the membrane obtained above approximated those shown in Table 1.

The membrane obtained as above was measured as to its deodorizing property vis-a-vis acetic acid as the simplest chemical compound for the lower fatty acid malodorous component. The method for measuring this property is as follows:

2.5 microliters of 2% aqueous acetic acid was placed in a 300 ml. Erlenmeyer flask. After the acetic acid had completely vaporized, a 10 cm. square of sample coated membrane was added thereto and the temperature maintained at 25° C. After 2 hours had elapsed, the residual acetic acid concentration in the flask was measured by a Kitagawa-type gas detector.

The result of the above measurement is as follows:

| Initial concentration | 44 ppm |
| --- | --- |
| Residual concentration | 0.5 ppm |

Work clothes and the like which are used in malodorous surroundings can be furnished with desirable waterproof and moisture permeability properties so as to provide comfort during work while wearing such clothes. Furthermore, it is possible to obtain a product which has odor-preventing properties and in which no unpleasant odors are left on the body of the wearer or on the wearer's undergarments. Such garments are highly useful in an industrial environment.

I claim:

1. A process for concentrating deodorant particles in a surface coating covering a membrane having continuous pores from one side of the membrane to the other, which comprises:
    (a) applying a surface coating to at least one side of said membrane, wherein the surface coating is a liquid coating material that contains particulate deodorant particles of an average particle diameter of about 1 micron, and wherein the continuous pores of the membrane have openings too small to allow passage of deodorant particles into the pores; and
    (b) allowing the liquid coating material to penetrate at least partially into the pores of the membrane, thus resulting in a greater concentration of particles in the resulting surface coating than in the originally applied coating material.

2. The process of claim 1 wherein said membrane comprises expanded polytetrafluoroethylene or porous polyolefin polymer membrane.

3. The process of claim 1 wherein said liquid coating material comprises polyether polyurethane resin or polymeric perfluorosulfonic acid resin.

4. The process of claim 1 wherein said deodorant is selected from the group consisting of a metallic hydroxide, a metallic oxide, a metal salt, and an organic acid.

* * * * *